United States Patent [19]
Noren et al.

[11] Patent Number: 5,417,715
[45] Date of Patent: May 23, 1995

[54] RATE RESPONSIVE HEART STIMULATION

[75] Inventors: Kjell Noren, Solna; Sven-Erik Hedberg, Kungsaengen; Pia Hagel, Sollentuna; Kurt Hoegnelid, Voesterhuninge, all of Sweden

[73] Assignee: Siemens Elema AB, Solna, Sweden

[21] Appl. No.: 132,815

[22] Filed: Oct. 7, 1993

[30] Foreign Application Priority Data

Oct. 7, 1992 [SE] Sweden ............... 92029370

[51] Int. Cl.⁶ .............................. A61N 1/365
[52] U.S. Cl. ........................................ 607/9
[58] Field of Search ............. 607/17, 18, 24, 23

[56] References Cited

U.S. PATENT DOCUMENTS

| | | |
|---|---|---|
| 4,535,774 | 8/1985 | Olson . |
| 4,686,987 | 8/1987 | Salo et al. . |
| 4,730,619 | 3/1988 | Koning et al. ............ 607/17 |
| 4,733,667 | 3/1988 | Olive et al. . |
| 4,802,481 | 2/1989 | Schroeppel . |
| 5,003,976 | 4/1991 | Alt . |
| 5,137,019 | 8/1992 | Pederson et al. . |
| 5,139,020 | 8/1992 | Koestner et al. . |
| 5,318,595 | 6/1994 | Ferek-Petric et al. ............ 607/17 |

FOREIGN PATENT DOCUMENTS 452732A 10/1991 European Pat. Off. ............ 607/18

Primary Examiner—William E. Kamm
Assistant Examiner—Marianne Parker
Attorney, Agent, or Firm—Hill, Steadman & Simpson

[57] ABSTRACT

A rate-responsive heart stimulator with a variable stimulation interval contains a measurement device which generates a measurement signal corresponding to the volume of blood in a heart during the blood-filling phase (diastole) and a comparator which compares the measurement signal with a defined threshold value corresponding to a defined degree of blood filling. The comparator generates a control signal when the measurement signal reaches the threshold value, the control signal representing the time elapsing since the last stimulation pulse, and controlling the heart stimulator's stimulation interval.

54 Claims, 3 Drawing Sheets

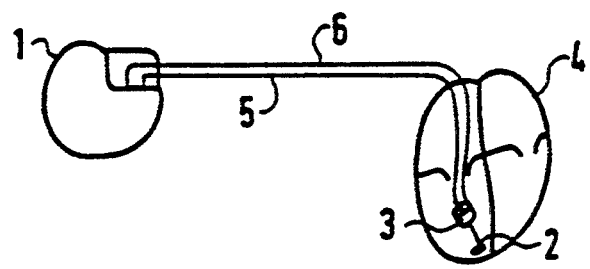
FIG 1
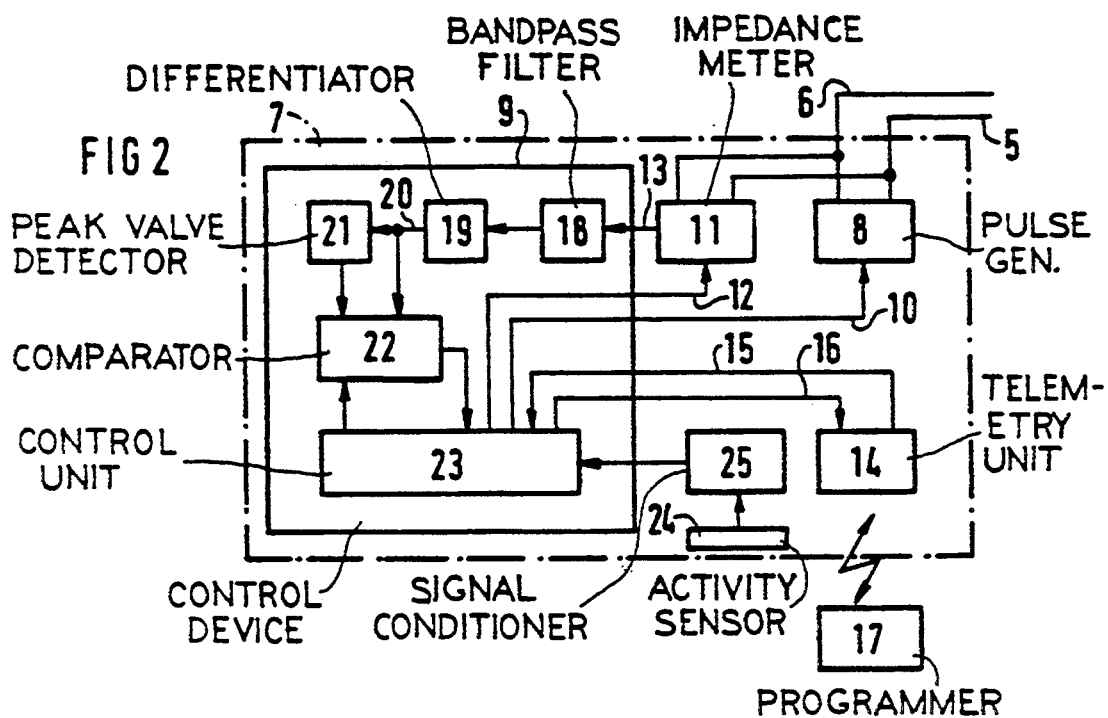
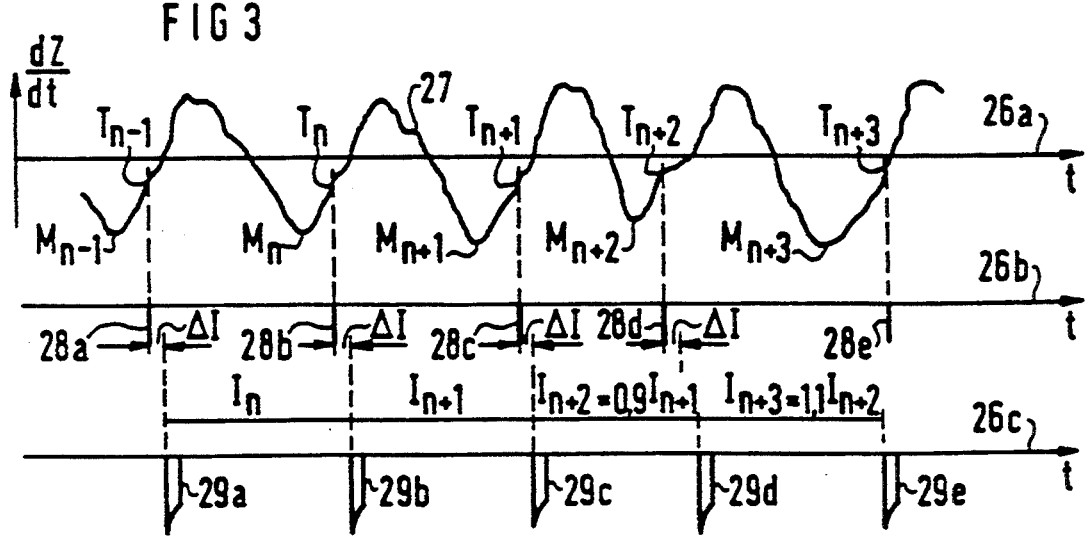

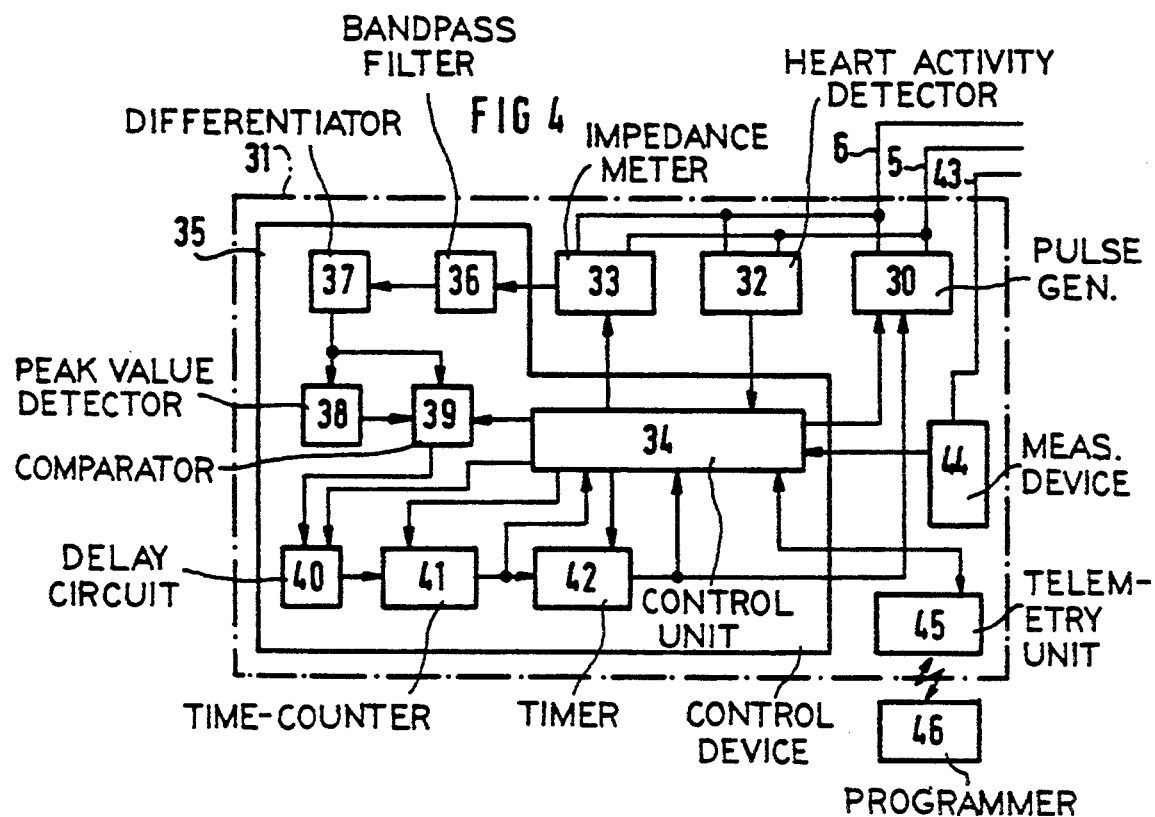
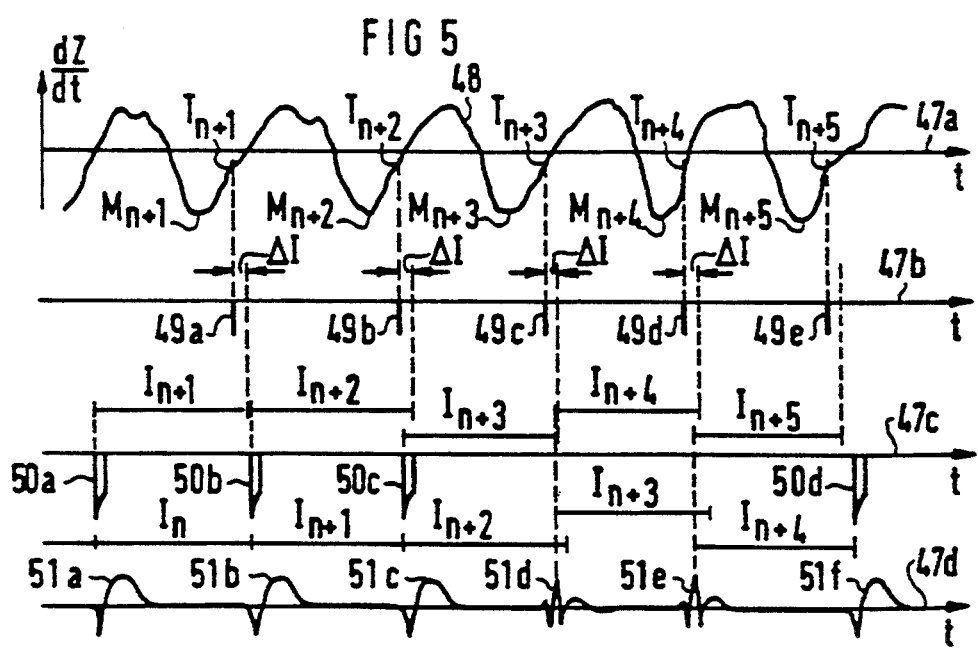

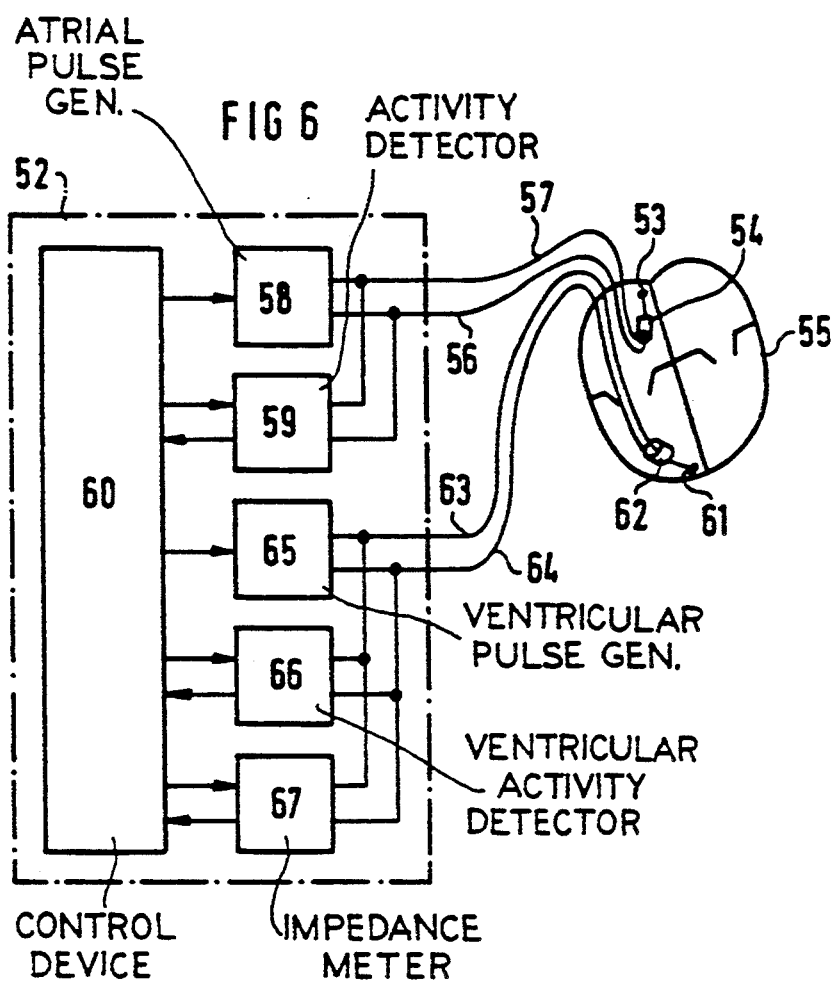

RATE RESPONSIVE HEART STIMULATION

BACKGROUND OF THE INVENTION

1. Field of the Invention

The present invention relates to a rate-responsive pacemaker of the type having at least one pulse generator which generates and emits stimulation pulses with a variable stimulation interval to a heart, a measurement device which generates a measurement signal corresponding to blood flow into or the volume of blood in a heart chamber, and a control device which controls the pulse generator's stimulation intervals depending on the measurement signal.

2. Description of the Prior Art

A known heart stimulator is described in U.S. Pat. No. 4,686,987 containing an impedance meter which measures heart impedance, a parameter which is proportional to ventricular volume and, accordingly, the volume of blood in the heart. The heart's stroke volume in each heart cycle is derived from the impedance signal, and the heart stimulator is controlled such that the stimulation rate causes the stroke volume to remain as constant as possible. In this known heart stimulator, any change in stroke volume thus indicates a change in the patient's level of physical activity and causes a change in the stimulation rate, thereby counteracting the change in stroke volume.

Another heart stimulator is described in U.S. Pat. No. 4,535,774 in which stroke volume is established either by measuring blood flow into the heart or by measuring impedance. The measured stroke volume is then used for setting a heartbeat rate. A relationship between stroke volume and heartbeat rate, in which stroke volume increases when the heartbeat rate increases, is utilized for optimizing cardiac function as much as possible, whereby the amount of blood pumped out of the heart every minute is sufficient for the body's needs without the heartbeat rate becoming excessively fast.

Both these known heart stimulators measure stroke volume and then utilize this parameter, or changes in same, for establishing an appropriate stimulation rate and then imposing that rate on the heart. The heart stimulator according to the former patent has the disadvantage that heartbeat rate rises rapidly when there is a need for a large volume of blood per unit of time (cardiac output). This problem is admittedly solved with a heart stimulator according to the latter patent in which stroke volume is allowed to change and increase when the heart rate increases, thereby retaining cardiac output without an excessively fast stimulation rate. In view of the normal course of events in a cardiac cycle, however, stroke volume is not particularly suitable for use in setting a heartbeat rate in this way. When blood in the heart has been expelled in a normal cardiac cycle and the muscle tissue relaxes for refilling, the influx of blood into the heart is governed by blood pressure in the vascular system. Blood flows rapidly into the heart at the beginning of diastole. The flow ultimately ceases when the heart is full of blood, i.e., when pressure in the heart and vascular system equalize. A slight change in stroke volume could therefore require a major change in rate. In addition, the influx of blood into the heart depends on the physical and mental condition of the person in whom the stimulation device is implanted. At rest, the influx of blood into a patient's heart is slower at the beginning of diastole than during physical exercise or stress.

SUMMARY OF THE INVENTION

An object of the invention is to provide a rate-responsive heart stimulator which effectively optimizes cardiac output on the basis of the volume of blood in the heart.

Such a heart stimulator is achieved in accordance with the principles of the present invention, which has a control device containing a comparator which, during the heart's blood-filling phase (diastole), compares a volume-indicative measurement signal with a defined threshold value corresponding to a defined degree of blood filling of the heart chamber and which generates a control signal when the measurement signal exceeds the threshold value. The control signal represents the time elapsed since the emission of the last stimulation pulse, and controls the pulse generator's stimulation interval.

This results in a heart stimulator which in essential respects imitates the function of a normal heart. The influx of blood into the heart at the start of diastole is slower when the body is at rest, and refilling time is therefore longer, corresponding to a slower rate. When the body is subjected to heavy physical exertion or mental stress causing the pressure of blood in the vascular system to rise, the rate of blood flow into the heart increases accordingly during diastole, as well as heartbeat rate. In contrast to known heart stimulators, it is not necessary for a heart stimulator according to the invention to calculate a heartbeat rate on the basis of stroke volume and then impose that rate on the heart. For example, measuring the flow of blood into the heart and using a threshold value corresponding to a predetermined flow value is sufficient. Since the flow of blood into the heart completely ceases when the heart has filled with blood, the threshold value corresponds to a specific degree of filling. Here, measuring blood flow in the latter part of diastole is enough to obtain the control signal.

In an embodiment of the heart stimulator in accordance with the invention, the comparator is connected to the pulse generator, and the pulse generator emits a stimulation pulse when it receives the control signal.

A heart stimulator operating according to this principle emits a stimulation pulse as soon as an adequate degree of blood filling is achieved in the heart.

Preferably the control device further contains means for delaying transmission of the control signal to the pulse generator by a defined delay interval. Operation is then more like the operation of a normal heart in which there is a delay between cessation of blood flow into the heart and a heartbeat. The delay interval also makes some variation in the stroke volume possible, since the flow of blood into the heart varies according to the level of activity. From the point at which the threshold value is reached until the delay interval has expired, the extra influx of blood will depend on the level of activity. In addition, a faster initial influx of blood during diastole increases myocardial stretching, thereby enabling the heart to receive more blood.

In this context, preferably the control device includes means for measuring the time elapsing between emission of the latest stimulation pulse and generation of the control signal and, if the defined delay interval were set by the control device, according to the time measured.

As an alternative to transmission of the control signal directly to the pulse generator, the heart stimulator according to the invention can be devised so the control device includes a time counter, which measures the time elapsing between the latest emitted stimulation pulse and the re-generation of the control signal, and a timer activated when a stimulation pulse is emitted and which times an entered stimulation interval, whereupon an activation signal is transmitted to the pulse generator which emits a stimulation pulse, the time measured then being fed to the timer to serve as the next stimulation interval.

As a result, the stimulation rate is be set with a delay, i.e., one stimulation interval. In this context, preferably the control device further includes means for changing, by a defined time interval, the time serving as the next stimulation interval. This makes it possible to monitor stimulation intervals in a different way than when the control signal is sent from the comparator straight to the pulse generator. Intervals could be prolonged or shortened, depending on their relationship to preceding intervals. This prevents rapid changes in the stimulation rate. A slow change in the rate when the level of activity changes is more like the way a healthy heart operates.

In this context, preferably the control device set the interval which changes the next stimulation interval depending on the time measured by the timer.

Alternatively the control device can include an averager, which forms a floating average of a defined number of preceding stimulation intervals, and the current average is sent to the timer to serve as the next stimulation interval.

Utilization of an average value governed by a defined number of preceding stimulation intervals ensures that excessively rapid changes in the stimulation interval are not imposed on the heart.

Preferably the control device measures impedance in the heart chamber, since the impedance signal is directly related to changes in the influx of blood.

In a further embodiment the control unit includes a differentiator which differentiates the measurement signal, and the comparator compares the differentiated measurement signal with the threshold value. The derivative of the impedance signal corresponds to the velocity of blood flow into the heart. This flow depends on the blood pressure gradient prevailing between the vascular system and the heart at the start of diastole when the myocardium relaxes. Influx is thus fastest at the beginning of diastole and slows thereafter. The derivative of the impedance signal therefore initially increases rapidly and approaches an extreme value. The derivative is negative when impedance is measured. The derivative then declines and approaches zero. The threshold value consists of a value passed by the derivative as it approaches zero after falling from its extreme value. Stroke volume and heart rate will vary in a natural way, since a faster initial flow causes the heart to fill with more blood at the same time as the stimulation interval is shortened.

In conjunction herewith, preferably the control device includes a peak value detector, which detects the derivative's extreme value during diastole, and also includes means for generating the threshold value so it constitutes a defined fraction of the extreme value.

The derivative's extreme value during diastole indicates the most rapid influx of blood into the heart, and this value is then utilized as the starting point for establishing a threshold value which designates a defined degree of heart filling. The extreme value corresponds to the derivative's minimum when impedance is measured. In this way, the function of the heart is made more independent of stroke volume as such and dependent on the phase of the heart's diastole. When the threshold value depends on the derivative's extreme value, function is additionally refined compared to the situation with a fixed threshold value. The threshold value could, e.g., be set at 25% of the derivative's extreme value.

In a further embodiment of the heart stimulator in accordance with the invention, the heart stimulator contains an additional measurement device, which measures a physiological variable, and means for determining the threshold value according to the physiological variable measured.

There are many known physiological variables which are affected in some way by the patient's level of activity, such as blood temperature, blood oxygen, respiratory rate, acceleration of the body in movement, etc. Utilization of a physiological variable in determining the threshold value results in more refined control of the heart stimulator. When the derivative of the measurement signal is employed as a parameter for blood filling, the physiological variable can be used for establishing how much of the derivative's extreme value the threshold value is to constitute. The heart stimulator also becomes more effective, since the physiological variable only affects the degree of filling to be achieved and does not supply a competitive stimulation rate.

To make the heart stimulator as safe as possible, the control device preferably includes a stimulation interval timer, which times each stimulation interval, and means for limiting the next stimulation interval so it does not become shorter than a first defined part of the timed stimulation interval, nor longer than the timed stimulation interval, by more than a second defined part of the timed stimulation interval.

Thus, a stimulation interval can be set at, e.g., 90–110% of the latest stimulation interval. This means that the rate is unable to change too quickly when there is a change in the level of activity.

DESCRIPTION OF THE DRAWINGS

FIG. 1 is a schematic illustration of a first embodiment of a heart stimulator according to the invention, connected to a heart.

FIG. 2 shows the first embodiment in greater detail in a block diagram

FIG. 3 illustrates the operation of the first embodiment of the heart stimulator in a diagram.

FIG. 4 shows a second embodiment of the heart stimulator in a block diagram.

FIG. 5 illustrates the operation of the second embodiment of the heart stimulator in a diagram.

FIG. 6 shows a third embodiment of a heart stimulator according to the invention in a block diagram.

DESCRIPTION OF THE PREFERRED EMBODIMENTS

The heart stimulator in FIG. 1 is a bipolar pacemaker 1, which has a tip electrode 2 and a ring electrode 3, respectively connected to a heart 4 via a first electrode conductor 5 and a second electrode conductor 6. The pacemaker 1 generates and emits stimulation pulses across the heart 4 through the electrodes 2 and 3 in order to counteract cardiac dysfunction in a patient.

A first embodiment of the pacemaker 1 is shown in FIG. 2, in a block diagram. Pacemaker electronics are contained in a pacemaker enclosure 7. A pulse generator 8 is connected to the first electrode conductor 5 and the second electrode conductor 6. The pulse generator 8 generates and emits stimulation pulses with a defined amplitude and duration. The time at which stimulation pulses are emitted, as well as the amplitude and duration of same, is controlled by a control device 9 to which the pulse generator 8 is connected by a stimulation pulse signal line 10. The design of the control device will be described in greater detail below.

An impedance meter 11 is also connected to the first electrode conductor 5 and the second electrode conductor 6 to measure impedance in the ventricle. The impedance meter intermittently emits a current pulse, e.g. a 5 µA pulse with a frequency of 4 kHz, between the tip electrode 2 and the ring 5 electrode 3. Voltage between the two electrodes 2 and 3 is measured, and a measurement signal is obtained which corresponds to impedance in the ventricle. Activation of the impedance meter 11 and the setting of the current pulse's amplitude and frequency are controlled by the control device 9, which is connected to the impedance meter 11 by a control line 12. The measurement signal is transmitted from the impedance meter 11 to the control device 9 via a signal line 13 for additional signal conditioning, as described below. Since blood has a lower impedance than heart tissue, the impedance signal will be at a minimum at the end of diastole and at a maximum at the end of systole.

In the control device 9, the measurement signal is fed from the impedance meter 11 to a bandpass filter 18 which filters out the part of the measurement signal corresponding to the volume of blood in the ventricle. The impedance meter 11 is active during at least a part of the heart's 4 blood-filling phase (diastole). The filtered measurement signal is differentiated in a differentiator 19 and sent through a signal line 20 to a peak value detector 21 and a comparator 22. The derivative becomes negative when impedance abates during diastole. The peak value detector 21 senses the derivative's minimum value and transmits this value to the comparator 22. The differentiated measurement signal is compared in the comparator 22 to a threshold value corresponding to optimum blood-filling at a defined stimulation point in time, and thus a defined stimulation interval. In this embodiment, the threshold value consists of a fraction of the derivative's peak value and is obtained from a control unit 23. This fraction can be set at, e.g., 25%, but the fraction of the derivative's minimum value which the threshold value constitutes is variable so pacemaker operation can be optimized. The pacemaker contains an activity sensor 24, a piezoelectric crystal glued to the inside of the enclosure 7 in this instance, for controlling the magnitude of this part. The piezoelectric crystal generates signals on the basis of changes in the pressure exerted against the enclosure 7 caused by body movements of the person in whom the pacemaker is implanted. The signal is transformed in a signal conditioner 25 into an activity signal which is sent to the control unit 23. The magnitude of the fraction is governed by the activity signal in such a way that the fraction is, e.g., 25% for rest and 40% when the level of activity is high. The fraction is set at a higher value when there is a high level of activity because the flow of blood in diastole is faster in high activity, making the derivative's minimum value more negative.

Thus, the differentiated measurement signal is compared in the comparator 22 with the measured minimum value for the derivative. When the differentiated measurement signal reaches the threshold value, a control pulse is generated by the comparator 22 and sent to the control unit 23. The control signal is delayed by the control unit 23, and the time elapsed between the latest stimulation pulse and the generation of the control pulse is compared to the latest stimulation interval. If the time, plus the delay, is shorter than a defined fraction of the latest stimulation interval, e.g. 90%, the control unit 23 does not send the control signal to the pulse generator 8 until the defined fraction of the last stimulation interval has expired. This is to prevent an excessively large increase in the rate of stimulation. In a corresponding manner, the control unit 23 sends a control signal to the pulse generator 8 if the comparator 22 fails to generate a control signal before the latest stimulation interval plus a second defined fraction of the latest stimulation interval, e.g. 10%, expires. The purpose is to keep the rate of stimulation from dropping too much when the level of activity declines. The control unit 23 also limits the rate of stimulation by only allowing rates within a specific interval, e.g. 60 to 170 beats/minute.

A telemetry unit is connected to the control device 9 by two signal conductors 15 and 16, and the control device 9 transmits information and program parameters, via the telemetry unit 14, to/from an extracorporeal programming unit 17 which a doctor can operate.

FIG. 3 illustrates in a diagram operation of the pacemaker in FIG. 2. Three time axes 26a–26c show the derivative 27 of the impedance signal Z, control signals 28a–28d from the comparator 22 and stimulation pulses 29a–29e from the pulse generator 8. For clarity, the derivative 27 is shown for the entire cardiac cycle, even though determination of the derivative 27 is only necessary for a part of diastole. Since blood is a better electrical conductor than heart tissue, impedance drops during diastole when the heart 4 fills with blood and increases during systole when the heart is emptied of blood. The derivative 27 therefore becomes negative during diastole and positive during systole. A minimum value $M_{n-1}$ for the derivative 27 is measured during diastole in the peak value detector 21. When the derivative signal approaches zero as the flow of blood into the heart 4 declines, it passes a threshold value $T_{n-1}$ constituting a specific part of the minimum value $M_{n-1}$. The comparator 22 then emits a control signal 28a which, after a preset delay ΔI, results in emission of stimulation pulse 29a. The emitted stimulation pulse 29a also starts a new stimulation interval $I_n$. A minimum value $M_n$ for the derivative signal 27 is again set during diastole, and a new control signal 28b is generated, when the threshold value $T_n$ is reached, leading to a new stimulation pulse 29b after the delay interval ΔI. The stimulation interval $I_{n+1}$ continues in the corresponding manner with the setting of the minimum value $M_{n+1}$, the passing of the threshold value $T_{n+1}$ which results in a control signal 28c and a stimulation pulse 29c after the delay interval I. During the stimulation interval $I_{n+2}$, the control signal 28d occurs so early in the interval $I_{n+2}$ that the stimulation interval $I_{n+2}$, even with the delay I, would be less than 90% of the last stimulation interval $I_{n+1}$ if a stimulation pulse were emitted after the delay I. Therefore, the stimulation pulse 29d is not emitted until 90% of the stimulation interval $I_{n-1}$ has elapsed. During the stimulation interval $I_{n+3}$, the opposite occurs. The comparator 22 has not generated any signal when 110% of the stimulation interval $I_{n+2}$ has elapsed, so a stimulation pulse 29e is emitted without the generation of any control signal. When the stimulation pulse 29e is emitted, the derivative rapidly passes the threshold value $T_{n+3}$, and the comparator 22 generates a control signal 28e which, however, is ignored by the control device 9.

A second embodiment of the pacemaker 1 is illustrated in FIG. 4. The tip electrode 2 and the ring electrode 3 are respectively connected by the first electrode conductor 5 and the second electrode conductor 6 to a pulse generator 30 in a pacemaker enclosure 31. A heart activity detector 32 and an impedance meter 33 are also connected to the first electrode conductor 5 and the second electrode conductor 6. The heart detector 32 senses the electrical activity of the heart 4 in order to detect any spontaneous heart responses and transmit information on same to a control unit 34 in a control device 35. Emission of a stimulation pulse is inhibited if any spontaneous response is detected in the heart.

The impedance meter 33 is controlled in the same way as the impedance meter 11 shown in FIG. 2, and thus generates a measurement signal which is transmitted to a bandpass filter 36 in the control device 35 for filtering out the part of the signal which corresponds to the volume of blood in the heart 4. The filtered signal is differentiated in a differentiator 37 and sent to a peak value detector 38 and a comparator 39. The derivative's minimum value is determined in the peak value detector and is also sent to the comparator 39. From the control unit 34, the fractional value governing the threshold value is sent to the comparator 39 in which it is compared to the differentiated measurement signal. An activity sensor, attached to the exterior of the pacemaker enclosure 31, is also employed in this embodiment and is connected by a sensor line 43 coupled to a measurement device 44 in the pacemaker 1. In this instance, the sensor could, e.g. be a thermometer or blood oximeter. The sensor signal is transformed in the measurement device 44 into an activity signal which is sent to the control unit 34 to change the partial value yielding the threshold value.

When the differentiated measurement signal reaches the threshold value, the comparator 39 generates a control signal which is sent to a delay circuit 40 and to the control unit 34. The delay circuit 40 transmits the control signal after a specific delay controlled by the control unit 34. Here, the delay depends on the interval to be prolonged, i.e. the control unit contains a timer which measures the time elapsing from the last stimulation or spontaneous event to generation of a control signal and, on the basis thereof, sets the prolongation as a given percent of the timed interval.

The delayed control signal is sent to a time-counter 41 and stops a time-count triggered by any signal emitted by the control unit 34, at the same time as a stimulation pulse or a detected spontaneous heart response. The timed interval serves as the duration of the next stimulation interval and is sent to the control unit 34 and to a timer 42.

The control unit 34 compares the measured time with the ongoing stimulation interval. If it is too short or too long, the measured time is adapted to the ongoing stimulation interval. Since the ongoing stimulation interval consists of the time measured for the last stimulation interval, this time is available in the control unit 34 for direct comparison. After the timer 42 times out the ongoing stimulation interval, a control pulse is sent to the control unit 34 and to the pulse generator 30, commanding the latter to emit a stimulation pulse. This overrides any subsequent control signal which may be generated as a result of the blood-filling comparison. Here, the control unit 34 activates the timer 42 which begins timing the timed interval, or an interval sent from the control unit 34, whereupon it serves as the stimulation interval.

If a spontaneous heart response is detected by the heart detector 32 before the timer 42 has timed out the stimulation interval, the control unit 34 sends an inhibitory signal to the pulse generator 30 and a signal to the timer 42, zeroing it, whereupon the timer begins timing the next stimulation interval.

A telemetry unit 45 communicates with the control unit 34 in the control device 35 and transmits information and program parameters to/from an extracorporeal programming unit 46.

FIG. 5 illustrates in a diagram the operation of the pacemaker 1 according to the second embodiment in FIG. 4. Four time axes 47a–47d show the impedance derivative 48, control signals 49a–49e, stimulation pulses 50a–50d and heart responses 51a–51f.

The stimulation pulse 50a on the time axis 47c induces a heart response 51a shown on time axis 47d. The stimulation pulse 50a also starts the stimulation interval $I_n$. The minimum negative derivative $M_{n+1}$ for the derivative signal 48 is reached during diastole, and the threshold value $T_{n+1}$ is reached when the derivative rises toward zero, whereupon a control signal 49a is generated by the comparator 39. A delay interval $\Delta I$ is added to the time elapsed between the last stimulation pulse 50a and the generation of the control signal 49a and the next stimulation interval $I_{n+1}$. When the stimulation interval $I_n$ expires, a stimulation pulse 50b is emitted which induces a heart response 51b and initiates timing of the stimulation interval $I_{n+1}$ and the stimulation interval $I_{n+2}$. The derivative's minimum value $M_{n+2}$ and signal transmission at the threshold value $T_{n+2}$ are set. A control signal 49b is generated, and the stimulation interval $I_{n+2}$, with the addition of the delay interval $\Delta I$, is set. When the stimulation interval $I_{n+1}$ expires, a stimulation pulse 50c is emitted which induces a heart response 51c. A spontaneous heart response 51d occurs during the stimulation interval $I_{n+2}$, so no stimulation pulse is emitted at the end of the stimulation interval $I_{n+2}$. However, the next stimulation interval $I_{n+3}$ is set in the same way as before, following determination of the minimum value $M_{n+3}$ and the threshold value $T_{n+3}$ by generation of the control signal 49c. A spontaneous heart response 51e also occurs in the stimulation interval $I_{n+3}$ before the stimulation interval $I_{n+3}$ elapses, and no stimulation pulse is emitted. However, the next stimulation interval $I_{n+4}$ is set in the same way as before. No spontaneous heart responses occur in the next stimulation interval $I_{n+4}$, so a stimulation pulse 50d is emitted when the stimulation interval $I_{n+4}$ elapses, inducing a heart response 51f. The next stimulation interval $I_{n-5}$ is simultaneously set in the same way as before.

Even in this embodiment, the set stimulation interval is compared with the latest stimulation interval in order to limit changes in the rate if, for example, a ventricular extrasystole (VES) occurs after half the stimulation interval, the set stimulation interval (i.e. the next interval) will amount to 90% of the present interval, not 50%.

An averager can be coupled between the time counter 41 and the timer 42 in FIG. 4 for calculating a running average value for a defined number of preceding stimulation intervals. Prolongation of the timed interval achieved by the delay circuit 40 can also be attained by measurement of the time elapsing between the stimulation pulse and generation by the comparator of the control signal, followed by addition of a fixed interval to the measured time before the signal is sent to the timer.

FIG. 6 shows a third embodiment of a heart stimulator according to the invention. Here, the heart stimulator is a bipolar dual chamber pacemaker 52. A first tip electrode 53 and a first ring electrode 54 are placed in the atrium of a heart 55 and are respectively connected to an atrial pulse generator 58 by a first electrode conductor 56 and a second electrode conductor 57. An atrial activity detector 59 is connected in parallel across the pulse generator 58. The atrial pulse generator 58 delivers stimulation pulses, controlled by the control device 60, to the atrium. The atrial activity detector 59 senses the atrium in order to detect any spontaneous atrial responses and sends such information to the control device 60, whereupon emission of an atrial stimulation pulse can be inhibited. The control device 60 controls the periods in which the atrial activity detector 59 is active.

In the corresponding manner, a second tip electrode 61 and a second ring electrode 62 are placed in the ventricle of the heart 55 and are respectively connected to a ventricular pulse generator 65 by a third electrode conductor 63 and a fourth electrode conductor 64. A ventricular activity detector 66 is connected in parallel across the ventricular pulse generator 65. The ventricular pulse generator 65 delivers stimulation pulses, controlled by the control device 60, to the ventricle. The ventricular activity detector 66 senses the ventricle in order to detect any spontaneous ventricular responses and sends such information to the control device 60, whereupon emission of an ventricular stimulation pulse can be inhibited. The control device 60 controls the periods in which the ventricular heart detector 59 is active.

The pacemaker 52 contains an impedance meter 67 to adapt delivery of stimulation pulses to the atrium and ventricle so the most natural heart rate possible is achieved.

Conditioning of the impedance signal by the control device 60 is as previously described in conjunction with FIGS. 2 and 4, i.e with filtration, differentiation and generation of a control signal when the derivative signal passes a threshold value dependent on the derivative's minimum value.

In the dual chamber pacemaker 52, a control signal is now used directly by the control device 60 for emitting an atrial stimulation pulse, without any delay, which, after an atrioventricular interval, is followed by a ventricular stimulation pulse. The atrial stimulation pulse provides an extra contribution of blood to the ventricle, resulting in a more natural contraction sequence for the heart. The ventricular stimulation pulse is inhibited if electrical conduction between the atrium and ventricle is working properly and the ventricle contracts spontaneously.

As in the previous embodiments of FIGS. 2 and 4, the dual chamber pacemaker 52 could also contain an activity sensor and a telemetry unit.

In the above embodiment, the derivative of the impedance signal is used for establishing the degree of filling. The impedance signal, with no differentiation, can alteratively be used for determining this parameter. Blood flow into the heart can even be used as a parameter as well.

Although modifications and changes may be suggested by those skilled in the art, it is the intention of the inventors to embody within the patent warranted hereon all changes and modifications as reasonably and properly come within the scope of their contribution to the art.

We claim as our invention:

1. A rate-responsive cardiac pacemaker comprising:
   electrode means for in vivo delivery of stimulation pulses to a heart;
   pulse generator means, connected to said electrode means, for emitting said stimulation pulses with a variable stimulation interval between successive stimulation pulses, said pulse generator means having a control input;
   measuring means for generating a measurement signal identifying an amount of blood present in a chamber of said heart as blood fills said chamber; and
   control means for supplying a control signal to said control input of said pulse generator means following emission of a latest stimulation pulse for controlling variation of said stimulation interval, said control means including comparator means for comparing said measurement signal to a threshold value corresponding to a defined degree of blood filling of said chamber and for generating an output signal when said measurement signal exceeds said threshold value, said control means supplying said control signal to said control input of said pulse generator means at a time, following emission of said latest stimulation pulse, dependent on said output signal.

2. A cardiac pacemaker as claimed in claim 1 wherein said comparator means has an output directly connected to said control input of said pulse generator means, said output signal serving as said control signal and said time being simultaneous with the generation of said output signal.

3. A cardiac pacemaker as claimed in claim 1 wherein said control means includes means for delaying transmission of said control signal to said pulse generator means by a defined delay interval after the generation of said output signal.

4. A cardiac pacemaker as claimed in claim 3 wherein said control means includes means for measuring a time elapsing between said latest stimulation pulse and the generation of said control signal, and means for setting said defined delay interval dependent on the time measured by said means for measuring a time.

5. A cardiac pacemaker as claimed in claim 1 wherein said control means includes a time counter means for measuring a time elapsing between said latest stimulation pulse and the generation of said control signal, timer means, activated upon the emission of said latest stimulation pulse, for timing out an entered stimulation interval and, at the end thereof, commanding said pulse generator means to emit a stimulation pulse, and means for entering the time measured by said time counter means into said timer means as a new entered stimulation interval for emitting for a next stimulation pulse.

6. A cardiac pacemaker as claimed in claim 5 wherein said control means includes means for changing said entered stimulation interval only by a defined time interval step.

7. A cardiac pacemaker as claimed in claim 6 wherein said control means includes means for setting a length of said defined time interval step dependent on the time measured by said time counter means.

8. A cardiac pacemaker as claimed in claim 1 wherein said control means includes a time counter means for measuring a time elapsing between said latest stimulation pulse and the generation of said control signal, timer means, activated upon the emission of said latest stimulation pulse, for timing out an entered stimulation interval and, at the end thereof, commanding said pulse generator means to emit a stimulation pulse, averaging means for forming a running average of the respective times measured by said time counter means for a selected number of preceding stimulation intervals, and means for entering a current value of said running average in said timer means as a new entered stimulation interval for emitting a next stimulation pulse.

9. A cardiac pacemaker as claimed in claim 8 wherein said control means includes means for changing said entered stimulation interval only by a defined time interval step.

10. A cardiac pacemaker as claimed in claim 9 wherein said control means includes means for setting a length of said defined time interval step dependent on said current value of said running average.

11. A cardiac pacemaker as claimed in claim 1 wherein said measurement means comprises means for measuring impedance in said chamber for generating a measurement signal corresponding to the volume of blood in said chamber.

12. A cardiac pacemaker as claimed in claim 1, further comprising:
further measurement means for measuring a physiological variable in vivo and for generating a further measurement signal corresponding to said physiological variable; and
means for setting said threshold value dependent on said further measurement signal.

13. A cardiac pacemaker as claimed in claim 1 wherein said control means includes stimulation interval timer means for timing each stimulation interval, and means for limiting a next stimulation interval so that said next stimulation interval is not shorter than a first selected portion of a preceding timed stimulation interval and is not longer than said preceding timed stimulation interval by more than a second defined portion of said preceding timed stimulation interval.

14. A rate-responsive cardiac pacemaker comprising:
electrode means for in vivo delivery of stimulation pulses to a heart;
pulse generator means, connected to said electrode means, for emitting said stimulation pulses with a variable stimulation interval between successive stimulation pulses, said pulse generator means having a control input;
measuring means for generating a measurement signal identifying an amount of blood present in a chamber of said heart as blood fills said chamber; and
control means for supplying a control signal to said control input of said pulse generator means following emission of a latest stimulation pulse for controlling variation of said stimulation interval, said control means including differentiator means for differentiating said measurement signal, comparator means for comparing the differentiated measurement signal to a threshold value corresponding to a defined degree of blood filling of said chamber and for generating an output signal when said differentiated measurement signal exceeds said threshold value, said control means supplying said control signal to said control input of said pulse generator means at a time, following emission of said latest stimulation pulse, dependent on said output signal.

15. A cardiac pacemaker as claimed in claim 14 wherein said control means further includes peak value detector means for detecting an extreme value of said differentiated measurement signal during said diastolic phase, and means for generating said threshold value as a defined fraction of said extreme value.

16. A cardiac pacemaker as claimed in claim 14 wherein said comparator means has an output directly connected to said control input of said pulse generator means, said output signal serving as said control signal and said time being simultaneous with the generation of said output signal.

17. A cardiac pacemaker as claimed in claim 16 wherein said control means includes means for delaying transmission of said control signal to said pulse generator means by a defined delay interval after the generation of said output signal.

18. A cardiac pacemaker as claimed in claim 17 wherein said control means includes means for measuring a time elapsing between said latest stimulation pulse and the generation of said control signal, and means for setting said defined delay interval dependent on the time measured by said means for measuring a time.

19. A cardiac pacemaker as claimed in claim 14 wherein said control means includes a time counter means for measuring a time elapsing between said latest stimulation pulse and the generation of said control signal, timer means, activated upon the emission of said latest stimulation pulse, for timing out an entered stimulation interval and, at the end thereof, commanding said pulse generator means to emit a stimulation pulse, and means for entering the time measured by said time counter means into said timer means as said entered stimulation interval for serving as the stimulation interval for a next stimulation pulse.

20. A cardiac pacemaker as claimed in claim 19 wherein said control means includes means for changing said entered stimulation interval only by a defined time interval step.

21. A cardiac pacemaker as claimed in claim 20 wherein said control means includes means for setting a length of said defined time interval step dependent on the time measured by said time counter means.

22. A cardiac pacemaker as claimed in claim 14 wherein said control means includes a time counter means for measuring a time elapsing between said latest stimulation pulse and the generation of said control signal, timer means, activated upon the emission of said latest stimulation pulse, for timing out an entered stimulation interval, and at the end thereof, commanding said pulse generator means to emit a stimulation pulse, averaging means for forming a running average of the respective times measured by said time counter means for a selected number of preceding stimulation intervals, and means for entering a current value of said floating average in said timer means as a new entered stimulation interval for emitting a stimulation pulse following said next stimulation pulse.

23. A cardiac pacemaker as claimed in claim 22 wherein said control means includes means for changing said entered stimulation interval only by a defined time interval step.

24. A cardiac pacemaker as claimed in claim 23 wherein said control means includes means for setting a length of said defined time interval step dependent on said current value of said running average.

25. A cardiac pacemaker as claimed in claim 14 wherein said measurement means comprises means for measuring impedance in said chamber for generating a measurement signal corresponding to the volume of blood in said chamber.

26. A cardiac pacemaker as claimed in claim 14, further comprising:
further measurement means for measuring a physiological variable in vivo and for generating a further measurement signal corresponding to said physiological variable; and
means for setting said threshold value dependent on said further measurement signal.

27. A cardiac pacemaker as claimed in claim 14 wherein said control means includes stimulation interval timer means for timing each stimulation interval, and means for limiting a next stimulation interval so that said next stimulation interval is not shorter than a first selected portion of a preceding timed stimulation interval and is not longer than said preceding timed stimulation interval by more than a second defined portion of said preceding timed stimulation interval.

28. A method for stimulating a heart comprising the steps of:
delivering of stimulation pulses in vivo to a heart;
emitting said stimulation pulses with a variable stimulation interval between successive stimulation pulses;
generating a measurement signal identifying an amount of blood present in a chamber of said heart;
comparing, during a diastolic phase of said heart, said measurement signal to a threshold value corresponding to a defined degree of blood filling of said chamber;
generating an output signal when said measurement signal exceeds said threshold value; and
varying said stimulation interval by emitting a next stimulation pulse at a time following emission of a latest stimulation pulse dependent on said output signal.

29. A method as claimed in claim 28 wherein the step of varying said stimulation interval is further defined by emitting said time simultaneously with the generation of said output signal.

30. A method as claimed in claim 28 wherein the step of varying said stimulation interval is further defined by emitting said next stimulation pulse after a defined delay interval following the generation of said output signal.

31. A method as claimed in claim 30 comprising the additional steps of:
measuring a measured time elapsing between said latest stimulation pulse and the emission of said next stimulation pulse; and
setting said defined delay interval dependent on said measured time.

32. A method as claimed in claim 28 comprising the additional steps of:
measuring an elapsed time elapsing between said latest stimulation pulse and the generation of said control signal;
timing out an entered stimulation interval starting upon the emission of said latest stimulation pulse;
commanding said pulse generator means, upon said entered stimulation interval being timed out, to emit a stimulation pulse; and
using said elapsed time as a new entered stimulation interval for a next stimulation pulse.

33. A method as claimed in claim 32 wherein the step of using the elapsed time as said new stimulation interval is further defined by changing said entered stimulation interval only by a defined time interval step.

34. A method as claimed in claim 33 comprising the additional step of setting a length of said defined time interval step dependent on said elapsed time.

35. A method as claimed in claim 28 comprising the additional steps of:
measuring an elapsed time elapsing between said last stimulation pulse and the generation of said control signal;
timing out an entered stimulation interval starting upon the emission of said latest stimulation pulse;
emitting said next stimulation pulse upon said entered stimulation interval being timed out;
forming a running average of the respective elapsed times measured for a selected number of preceding stimulation intervals; and
using a current value of said running average as a new entered stimulation interval for emitting a stimulation pulse following said next stimulation pulse.

36. A method as claimed in claim 35 wherein the step of using said current value of said running average as a new entered stimulation interval is further defined by changing said entered stimulation interval only by a defined time interval step.

37. A method as claimed in claim 36 comprising the additional step of setting a length of said defined time interval step dependent on said current value of said running average.

38. A method as claimed in claim 28 wherein the step of generating a measurement signal is further defined by generating an impedance signal corresponding to the volume of blood in said chamber.

39. A method as claimed in claim 28, comprising the additional steps of:
measuring a physiological variable in vivo and generating a further measurement signal corresponding to said physiological variable; and
setting said threshold value dependent on said further measurement signal.

40. A method as claimed in claim 28 comprising the additional steps of:
timing each stimulation interval; and
limiting a next stimulation interval so that said next stimulation interval is not shorter than a first selected portion of a preceding timed stimulation interval and is not longer than said preceding timed stimulation interval by more than a second defined portion of said preceding timed stimulation interval.

41. A method for stimulating a heart comprising the steps of:
delivering stimulation pulses in vivo to a heart;
emitting said stimulation pulses with a variable stimulation interval between successive stimulation pulses;
generating a measurement signal identifying an amount of blood present in a chamber of said heart;
differentiating said measurement signal;
comparing, during a diastolic phase of said heart, the differentiated measurement signal to a threshold value corresponding to a defined degree of blood filling of said chamber;

generating an output signal when said differentiated measurement signal exceeds said threshold value; and varying said stimulation interval by emitting a next stimulation pulse at a time following emission of a latest stimulation pulse dependent on said output signal.

42. A method as claimed in claim 41 comprising the additional steps of:

detecting an extreme value of said differentiated measurement signal during said diastolic phase; and generating said threshold value as a defined fraction of said extreme value.

43. A method as claimed in claim 41 wherein the step of varying said stimulation interval is further defined by emitting said next stimulation pulse simultaneously with the generation of said output signal.

44. A method as claimed in claim 43 wherein the step of varying said stimulation interval is further defined by emitting said next stimulation pulse after a defined delay interval following the generation of said output signal.

45. A method as claimed in claim 44 comprising the additional steps of:

measuring a measured time elapsing between said latest stimulation pulse and the emission of said next stimulation pulse; and setting said defined delay interval dependent on said measured time.

46. A method as claimed in claim 41 comprising the additional steps of:

measuring an elapsed time elapsing between said latest stimulation pulse and the generation of said control signal;

timing out an entered stimulation interval starting upon the emission of said latest stimulation pulse;

emitting said next stimulation pulse upon said entered stimulation interval being timed out; and using said elapsed time as a new entered stimulation interval for a stimulation pulse following said next stimulation pulse.

47. A method as claimed in claim 46 wherein the step of using said elapsed time as said new stimulation interval is further defined by changing said entered stimulation interval only by a defined time interval step.

48. A method as claimed in claim 47 comprising the additional step of setting a length of said defined time interval step dependent on said elapsed time.

49. A method as claimed in claim 41 comprising the additional steps of:

measuring an elapsed time elapsing between said last stimulation pulse and the generation of said control signal;

timing out an entered stimulation interval starting upon the emission of said latest stimulation pulse;

emitting said next stimulation pulse upon said entered stimulation interval being timed out;

forming a running average of the respective elapsed times measured for a selected number of preceding stimulation intervals; and using a current value of said running average as a new entered stimulation interval for emitting a stimulation pulse following said next stimulation pulse.

50. A method as claimed in claim 49 wherein the step of using said current value of said running average as said new entered stimulation interval is further defined by changing said entered stimulation interval only by a defined time interval step.

51. A method as claimed in claim 50 comprising the additional steps of setting a length of said defined time interval step dependent on said current value of said running average.

52. A method as claimed in claim 41 wherein the step of generating a measurement signal is further defined by generating an impedance signal corresponding to the volume of blood in said chamber.

53. A method as claimed in claim 41, comprising the additional steps of:

measuring a physiological variable in vivo and generating a further measurement signal corresponding to said physiological variable; and setting said threshold value dependent on said further measurement signal.

54. A method as claimed in claim 41 comprising the additional steps of:

timing each stimulation interval; and limiting a next stimulation interval so that said next stimulation interval is not shorter than a first selected portion of a preceding timed stimulation interval and is not longer than said preceding timed stimulation interval by more than a second defined portion of said preceding timed stimulation interval.

* * * * *